(12) United States Patent
Gugler et al.

(10) Patent No.: US 11,957,590 B2
(45) Date of Patent: Apr. 16, 2024

(54) SHELL TO BE DRIVEN INTO A BONE SUBSTANCE FOR A PROSTHETIC JOINT

(71) Applicant: MATHYS AG BETTLACH, Bettlach (CH)

(72) Inventors: Christian Gugler, Frauenfeld (CH); Armin Jossi, Frauenfeld (CH); Martin Schmidt, Warth (CH); Andreas Meyenhofer, Schlattingen (CH)

(73) Assignee: MATHYS AG BETTLACH, Bettlach (CH)

( * ) Notice: Subject to any disclaimer, the term of this patent is extended or adjusted under 35 U.S.C. 154(b) by 540 days.

(21) Appl. No.: 16/972,662

(22) PCT Filed: Nov. 19, 2019

(86) PCT No.: PCT/EP2019/081702
§ 371 (c)(1),
(2) Date: Dec. 7, 2020

(87) PCT Pub. No.: WO2020/109060
PCT Pub. Date: Jun. 4, 2020

(65) Prior Publication Data
US 2021/0275309 A1    Sep. 9, 2021

(30) Foreign Application Priority Data
Nov. 28, 2018   (EP) .................................. 18208744

(51) Int. Cl.
*A61F 2/34*      (2006.01)
*A61F 2/30*      (2006.01)
*A61F 2/40*      (2006.01)

(52) U.S. Cl.
CPC ............ *A61F 2/34* (2013.01); *A61F 2/30771* (2013.01); *A61F 2/4014* (2013.01);
(Continued)

(58) Field of Classification Search
CPC ...... A61F 2/34; A61F 2/4014; A61F 2/30771; A61F 2002/30879; A61F 2002/30884;
(Continued)

(56) References Cited

U.S. PATENT DOCUMENTS 6,231,612 B1    5/2001    Balay et al.
7,018,417 B2    3/2006    Kuoni et al.
(Continued)

FOREIGN PATENT DOCUMENTS

DE    10 2006 017 473 A1    10/2007
EP        1 411 869 B1       5/2005
(Continued)

OTHER PUBLICATIONS

International Search Report Corresponding to PCT/EP2019/081702 dated Apr. 20, 2020.
(Continued)

*Primary Examiner* — Brian A Dukert
(74) *Attorney, Agent, or Firm* — NIXON PEABODY LLP (57) ABSTRACT

A shell (1) for a prosthetic joint to be driven into a bone substance. The shell having an outer lateral surface (4) which is convexly curved in cross section and on which a plurality of ribs (5) is arranged. All ribs extend in the same direction at a preferably increasing gradient angle of 45° to 85° at the equatorial end (6) to a pole-side end (7). The cumulative flank projection area of all ribs (5) corresponds to at least a fifth of the entire outer lateral surface. As a result of this measure, a very high primary stability is achieved once the shell has been driven in, the shell being screwed into the bone substance very precisely and without bone material being sheared off. This arrangement can also be applied, similarly, to a concavely curved inner lateral surface.

27 Claims, 9 Drawing Sheets

(52) U.S. Cl.
CPC ............... *A61F 2002/30879* (2013.01); *A61F 2002/3425* (2013.01); *A61F 2002/4018* (2013.01)

(58) Field of Classification Search
CPC .. A61F 2002/30886; A61F 2002/30904; A61F 2002/3425; A61F 2002/4018
See application file for complete search history.

(56) References Cited

U.S. PATENT DOCUMENTS

| | | |
|---|---|---|
| 9,198,761 B2 | 12/2015 | Gugler et al. |
| 2010/0063596 A1 | 3/2010 | Imhof |

FOREIGN PATENT DOCUMENTS

| | | |
|---|---|---|
| EP | 1 806 112 A1 | 7/2007 |
| EP | 2 502 604 A1 | 9/2012 |

OTHER PUBLICATIONS

Written Opinion Corresponding to PCT/EP2019/081702 dated Apr. 20, 2020.

SHELL TO BE DRIVEN INTO A BONE SUBSTANCE FOR A PROSTHETIC JOINT

This application is a National Stage completion of PCT/EP2019/081702 filed Nov. 19, 2019, which claims priority from European patent application serial no. 18208744.5 filed Nov. 28, 2018.

FIELD OF THE INVENTION

The invention relates to a shell to be driven into or onto a bone substance for a prosthetic. Such shells are also called drive-in sockets, which are, in contrast to screwed-in or cemented sockets, driven into a previously milled-out recess in the bone. What occurs when the condition of the bone substance is good is sufficient primary stability until the subsequently commencing bone growth on the socket surface additionally stabilizes the prosthesis.

BACKGROUND OF THE INVENTION

EP 1 411 869 B1 disclosed a so-called press-fit socket which is to be driven in and in which at least two locking elements are arranged on the exterior of the socket base body, each comprising a drive-in web. From the distal start of the web up to the proximal end of the web, said drive-in web defines at least a pitch of 85° to 60° based on the base, this corresponding to an angle of twist of 5° to 30°. A disadvantage of this known joint socket is that the drive-in webs, which are few and are relatively large in relation to the socket size, still do not yield optimal primary stability. In addition, the drive-in webs are designed as locking elements, and, according to a particularly preferred embodiment, this is achieved by the pitch of the drive-in webs continuously increasing toward the pole-sided end. This results in the socket shell being jammed or locked in the hip bone after being driven in, with the result that screw-out against the drive-in direction is prevented in an effective manner. This type of jamming or locking also results in some of the bone material being plowed away when the joint shell is driven in, this creating a bone groove which is no longer completely filled up by the drive-in web, this, however, weakening in turn the anchoring that is striven for.

SUMMARY OF THE INVENTION

It is therefore an object of the present invention to provide a shell of the type mentioned at the start which achieves an improved primary stability and which can be driven in or driven on as gently as possible without the occurrence of cavities or shears in the bone material. The surface of the shell should achieve a good osteoinductive effect, this aiming at long-term fixation by osteointegration. In addition, novel application areas, for example for shaft-free prosthetic shoulders, are to be opened up by the shell as well.

According to the invention, this object is achieved using a shell having the features in the independent claim(s). The shell has, then, an outer lateral surface which is convexly curved, especially spherical, in cross-section, especially based on the longitudinal central axis of said shell, or an inner lateral surface which is concavely curved, especially spherical, on which outer or inner lateral surface there is arranged a plurality of ribs, wherein all ribs extend in the same direction under a preferably increasing pitch angle from 45° to 85° at the equatorial end toward a pole-sided end on the outer lateral surface. The course of the ribs is preferably chosen such that each rotation by a predetermined angular value brings about a constant advance of the socket. What is brought about said course is that the socket, when driven in, automatically rotates by a few angular degrees in a specified manner. In this connection, the pitch angle is understood to mean the angle in a cylindrical projection, this being, by analogy with screw threads, the angle enclosed by the circumference and by the helical curve. In contrast, the pitch is the longitudinal displacement in the axial direction per revolution or per identical rotation angle.

Each rib has a certain interrupted or uninterrupted rib length and a certain unvarying or varying rib height and also two flank surfaces. Each rib has a flank projection area which is based on a plane running through the longitudinal extent of the rib and perpendicularly to the outer lateral surface or to the inner lateral surface. Said flank projection area of a rib is the projection area independent of the cross-sectional configuration of the rib and independent of the flank inclination, but with consideration of interruptions and indentations. What is regarded as the outer lateral surface or inner lateral surface is the actual outer surface or inner surface of a shell from the equator up to the pole, but without consideration of mounting holes or other openings. The sum of the flank projection areas of all ribs corresponds to at least one fifth of the entire outer lateral surface or the entire inner lateral surface. The lateral surfaces can, in cross-section, also be ellipsoidal in a plane containing the axis.

As a result of the specified ratio of the total flank projection area to the outer lateral surface or to the inner lateral surface, what is achieved for all shells independent of their use, purpose or size is an optimal form fit with the bone and hence also an optimal primary anchoring. At the same time, it is evidently possible to vary the number of ribs, the rib length and the rib height in order to achieve at least the desired minimum cumulative flank projection area. The mounting of the ribs on the inner lateral surface and the optimized primary anchoring allow, for example, the use of the shell for shaft-free prosthetic surface replacements (bone resurfacing) especially of the hip joint or the shoulder joint.

It is evident that the design and number of ribs and hence also the achievable flank projection area reaches orthopedic and also production-related limits in the case of the common prosthetic joints. Therefore, particularly advantageously, the ratio between the sum of the projection area of all ribs and the outer lateral surface or at the inner lateral surface is in the range from 0.2:1 to 1:1. It is evident therefrom that the sum of the projection areas can be readily equally great to the outer lateral surface or the inner lateral surface of the actual shell or calotte.

In this connection, at least 20 and preferably between 30 and 80 ribs can be arranged on the outer lateral surface or the inner lateral surface. This number of ribs yields a balanced ratio with regard to the dimensioning of the ribs and the distribution thereof on the outer lateral surface or on the inner lateral surface.

The interval between adjacent ribs at the equatorial end from rib center to rib center on the outer lateral surface or on the inner lateral surface (radian measure) is preferably in the range from 0.2 mm to 4 mm, particularly preferably in the range from 1 mm to 3.5 mm, and this can evidently lead to a high number of ribs in the case of the common nominal shell sizes for hip-joint shells of between 46 mm and 68 mm and depending on the rib height.

Preferably, the cumulative length of all ribs is also additionally at least 1000 mm or more. Self-evidently, it is not ruled out by this configuration of the socket that, for example, individual additional elements such as cams or fins are additionally arranged in addition to the ribs in the equatorial region.

Ideally, the ratio of rib interval to rib height is between 5:1 to 1:1. However, in the case of a rib interval of, for example, 0.2 mm, it is also possible to arrange only ribs of a relatively small height. Self-evidently, shell size also plays a major role here. The cumulative flank projection area can turn out differently depending on shell size, rib interval and rib height. What is regarded here as the interval between adjacent ribs is the interval between the center thereof on the outer lateral surface or on the inner lateral surface at the equatorial end. At the same time, it is conceivable that the total outer lateral surface or inner lateral surface is, based on the latitudes, not provided with ribs. This evidently yields relatively large gaps in the rib-free sector, which gaps are not regarded as the distance between adjacent ribs.

Further advantages can be achieved when at least 30%, preferably at least 50%, of the ribs extend over more than half the height of the joint socket, based on the longitudinal central axis thereof. It is evident that the ribs converge toward the pole region, this continuously reducing the interval between the ribs. To nevertheless ensure a sufficient rib interval at all positions in the case of a given rib height, it is therefore appropriate when some of the ribs, typically half of the ribs, extend toward the pole region only up to a certain latitude, whereas the remaining ribs are additionally further guided as far as into the proximity of the pole. Alternatively, the rib height can also be varied in the course of the ribs.

Advantageously, ribs of differing length are arranged on the outer lateral surface or on the inner lateral surface, specifically preferably in a regular sequence based on the circumference. However, irregular patterns would also be conceivable in certain cases, wherein, for example, a few ribs extend as far as into the proximity of the pole, whereas multiple substantially shorter ribs are arranged between two long ribs.

Advantageously, the rib height is in the range from 0.1 mm to 4 mm, though said height is self-evidently also dependent on the chosen average interval between the ribs and on the shell size. At the same time, it may also be advantageous when ribs of differing height are arranged, preferably in a regular sequence, on the outer lateral surface or on the inner lateral surface.

Furthermore, the rib arrangement can be varied by ribs of differing rib height being arranged on a certain latitude based on the circumference of the outer lateral surface or the inner lateral surface.

To bring about a displacement of bone material that is as gentle as possible, the ribs advantageously have a cross-section which tapers from the rib foundation toward the rib vertex, preferably a wedge-shaped cross-section. As an alternative to a wedge-shaped cross-section, it could also run in a trapezoidal or pagoda-shaped or peninsula-shaped manner. However, it would also be conceivable in certain cases for the rib flanks to run approximately in parallel, meaning that the ribs obtain a rectangular configuration. Furthermore, it may be advantageous to vary the cross-sectional profile of the ribs, based on the length thereof, in a continuous manner or in steps. The cross-sections mentioned are based on a plane perpendicular to the longitudinal extent of the rib and perpendicular to the outer lateral surface or to the inner lateral surface.

Advantageously, the course of the rib pitch is chosen such that drive-in in the drive-in direction involves the movement of each segment of a rib in the groove which is grooved by a preceding segment, meaning that drive-in is not followed by any jamming or blocking in the bone material. At the same time, the pitch curve of the ribs must evidently take account of the shell curvature such that the result is a thread-like course, wherein the ribs imprint complementary threaded grooves into the bone material and the bone material thereby obtains the function of a threaded nut. This measure prevents bone material from being sheared off or plowed away during drive-in, this evidently being detrimental to primary stability.

Primary stability after the joint shell has been driven in can be further increased by the flanks of the individual ribs having different roughness values, such that the flanks subjected to a greater load during drive-in have the lower roughness value than the flanks subjected to a greater load during pull-out. This produces an increased self-locking of the joint shell without the occurrence of jamming or blocking as in the prior art. The different roughness values merely bring about an increase in friction on one flank side in each case.

Further considerable advantages with respect to primary stability can be achieved when at least some of the ribs are interrupted to form individual rib teeth. An individual rib then evidently forms a row of teeth arranged one after another. Depending on the configuration of said teeth, this facilitates drive-in and hampers lever-out or pull-out. Since the effect of the ribs in the equator region is evidently different from in the pole region, it is also appropriate when the rib teeth of a rib have a differing configuration between the equatorial end and the pole-sided end.

The rib teeth preferably form irregular, multisurface bodies having a quadrangular footprint, two flank sides inclined against one another, having a pole side facing the pole and having an equator side facing the equator, wherein the pole side preferably encloses a smaller angle with the outer lateral surface or with the inner lateral surface of the shell than the equator side. As a result, the equator side forms an obstruction surface or barbed surface, especially when it is at an angle of approx. 90° or more on the outer lateral surface or on the inner lateral surface. In contrast, the pole side prevents cutting of the bone material with the flatter angle, and displacement of the bone material is achieved. As a result, drive-in of the shell is gentle to the bone, and a high primary stability is achieved.

Further advantages can be achieved when the successive rib teeth of a rib are configured such that a displacement of bone material takes place in the drive-in direction and an anchoring in the bone material takes place in the screw-out direction. Such an effect can, for example, be achieved by setting the rib teeth, with the individual rib teeth being arranged slightly offset to one another in an alternating and preferably unilateral manner.

To further facilitate penetration of the ribs into the bone material, it is advantageous when at least some of the rib teeth have, based on the course of the rib, a cross-section which is triangular in the near-pole region and trapezoidal in the equatorial region. In this connection, the triangular rib teeth which go in front during drive-in cut the grooves, whereas the trapezoidal rib teeth which follow bring about a build-up of tension in the grooves that is as optimal as possible.

It is advantageous when the gaps between the rib teeth do not extend as far as the outer lateral surface or as far as the inner lateral surface. The penetration and exact guidance of the rib teeth in the grooved bone groove is improved if a continuous rib body remains, even if said body itself only has a very small height.

To improve secondary stability, the outer lateral surface or the inner lateral surface and/or the ribs can be provided with an osteoinductive coating in full or in part. Coatings of this type are already known per se in the prior art. In this connection, the coating can, for example, be a titanium plasma coating or else a hydroxyapatite coating. Possible shell materials are titanium and titanium alloys, but also Fe and Co alloys as per ISO5832 or ceramics or polymer materials. The joint sockets according to the invention can be produced by forming, machining and/or by additive manufacturing processes.

The shell according to the invention can be a joint socket for a prosthetic hip joint to be driven into an acetabulum. Alternatively, the shell can, however, also be a component of a shaft-free prosthetic shoulder joint, wherein the shell is a humeral anchor to be driven into a humerus. In principle, it would be also additionally possible for the shell to assume other anchoring functions for prostheses on bone structure. In the case of a joint socket for a prosthetic hip joint, the ratio between the sum of the flank projection area of all ribs and the outer lateral surface can be in the range from 0.2:1 to 0.8:1. In contrast, the ratio in the case of a shell for a humeral anchor is more in the range from 0.3:1 to 1:1. This difference between the ratios is because of the smaller shell diameter in the case of the humeral anchor and the resultant smaller outer lateral surface.

In the case of hip-joint sockets, the number of ribs is ideally in the range between 40 and 70 ribs depending on the socket size. However, this number can be fallen short of in the case of shells for prosthetic shoulder joints and be in the range from 30 to 40 ribs.

A further parameter for the shell design according to the invention can be the ratio between the rib height and the diameter of the outer lateral surface or the inner lateral surface. Consequently, it is particularly advantageous when the ratio between the rib height from the rib foundation to the rib vertex and the diameter of the outer lateral surface or the inner lateral surface at the equator is in the range from 0.001:1 to 0.150:1, preferably in the range from 0.01:1 to 0.04:1.

BRIEF DESCRIPTION OF THE DRAWINGS

Further individual features and advantages of the invention are revealed by the exemplary embodiments described below and by the drawings, where:

FIG. 1, FIG. 3: shows a perspective view of the joint socket as per FIG. 1, FIG. 4: shows one half of a schematically represented side view containing different rib teeth, FIG. 12, FIG. 14: shows the schematic representation of a prosthetic hip joint in the acetabulum, FIG. 16: shows a side view of the broad side of a humeral anchor with ellipsoidal cross-section, FIG. 17: shows a side view of the narrow side of the humeral anchor as per FIG. 16, FIG. 18: shows a top view of the humeral anchor as per FIG. 16, FIG. 19: shows a cross-section through the plane I-I of the humeral anchor as per FIG. 18, FIG. 20: shows a schematic and greatly enlarged perspective view of a rib with drawn-in flank projection area.

DETAILED DESCRIPTION OF THE PREFERRED EMBODIMENTS

Figure 1:
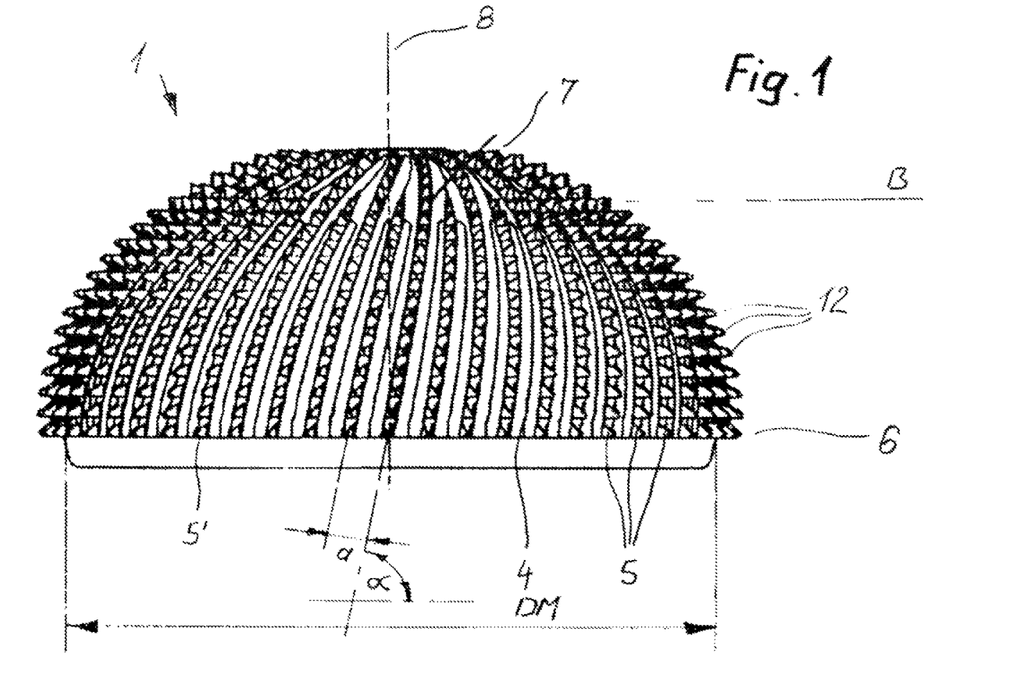
FIG. 1: shows the side view of a greatly enlarged representation of a joint socket.
Figure 2:
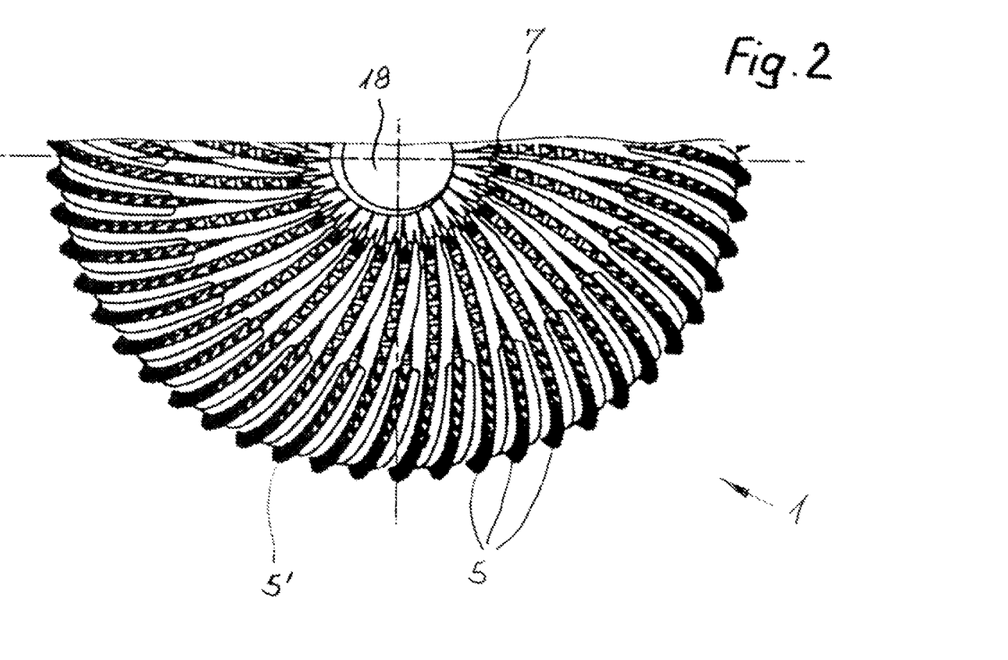
FIG. 2: shows one half of a top view of the joint socket as per
Figure 3:
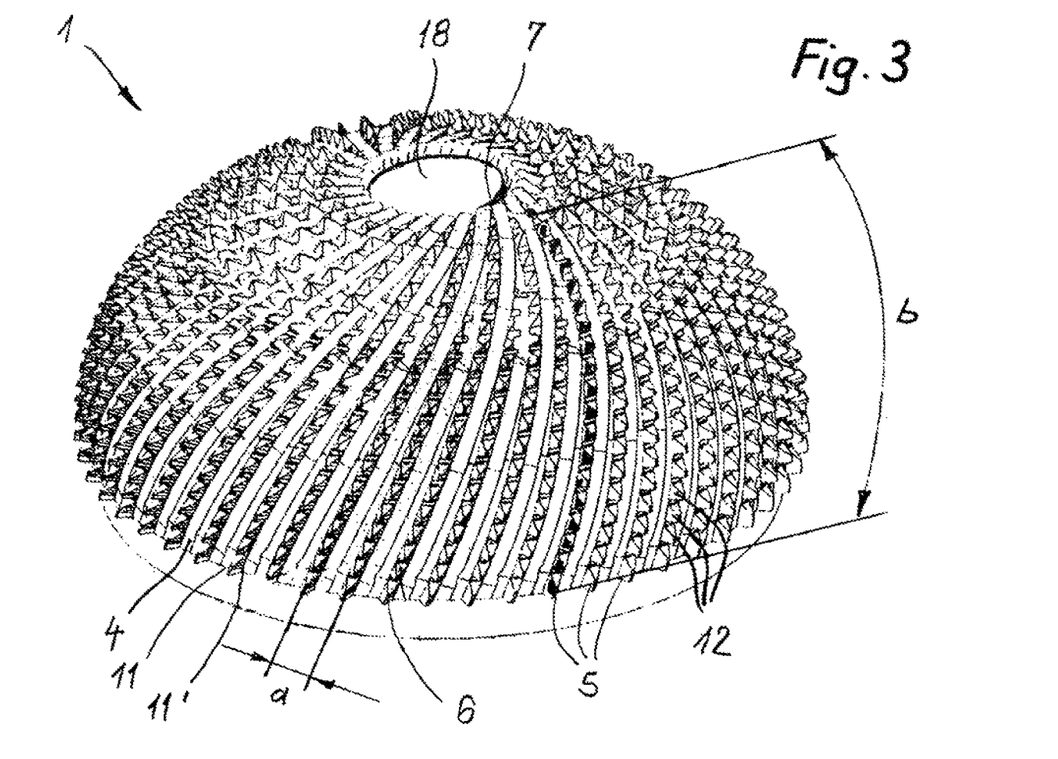

As depicted in FIGS. 1 to 3, a joint socket 1 consists of a shell-shaped body having an outer lateral surface 4 on which a plurality of ribs 5 are arranged distributed over the entire circumference. They extend from an equatorial end 6 up to a pole-sided end 7. The joint socket is flatted in the pole region and a pole opening 18 is arranged on the longitudinal central axis 8. Each individual rib consists of a plurality of rib teeth 12 arranged one after another. In addition, not all ribs run as far as into the proximity of the pole. Every second rib 5' only extends up to a latitude B, which is somewhat further from the pole. At the equator, the hemispherical shell has a shell diameter DM which is somewhat larger than the diameter of the cutter with which the bone substance is milled out.

The distance a between two ribs, based in each case on the center of an individual rib at the rib foundation, is greatest at the equatorial end and decreases toward the pole-sided end. As mentioned in the introduction, said distance is between 0.2 mm to 4 mm. The pitch angle α is in the range from 45° to 85° at the equator and increases toward the pole.

The length b of a rib is based in each case on the spatial course thereof or on the development thereof, as depicted in FIG. 3. The cumulative length of all ribs is therefore yielded by the addition of the length of all ribs, irrespective of whether a mixture of longer and shorter ribs is concerned.

Each rib has rib flanks 11 and 11' on two sides. The flank projection area P of a rib is yielded by the rib length b multiplied by the rib height d or by the averaged rib height, if said rib height varies over the length of the rib, minus the gaps between the teeth. Using this type of calculation, what is evidently ascertained is the net projection area of a rib flank without taking the inclination and curvature thereof into account. The projection area is, however, that area which plays the greatest role with regard to primary stability. Altogether, the cumulative flank projection area of a socket is thus calculated from the number of ribs multiplied by the flank projection area of an individual rib.

Figure 4:
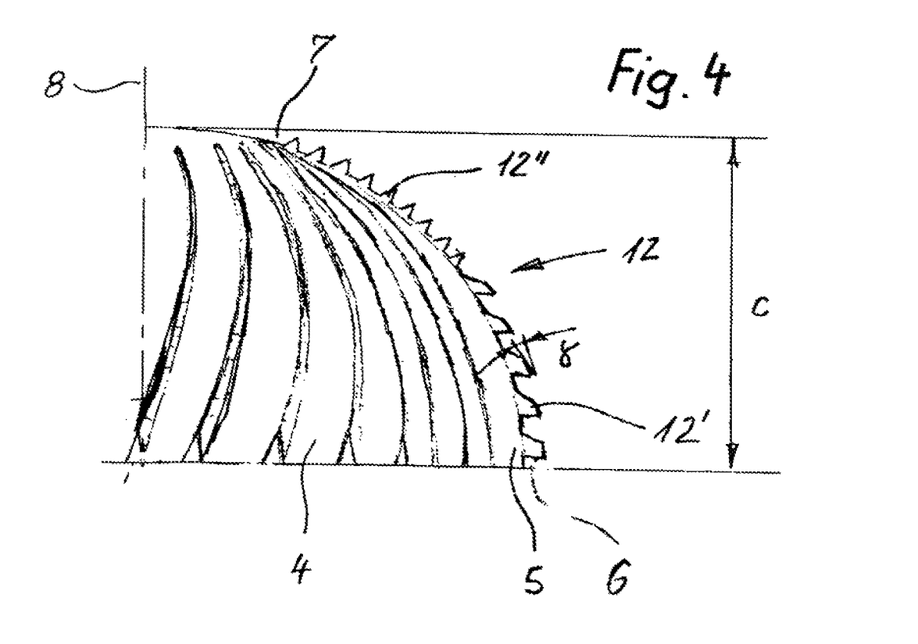

Details of a rib profile are depicted in FIG. 4. Here, the ribs are divided into individual rib teeth 12, with rib teeth 12' which are trapezoidal in cross-section being arranged in the near-equatorial region about as far as half of the joint socket height c. In the near-pole region, the rib teeth 12" have a triangular cross-section. The cross-section is, then, based on the longitudinal extent of a rib from the near-equatorial end 6 up to the pole-sided end 7. The trapezoidal rib teeth 12' have a clearance angle γ on their vertex line in relation to the radius of curvature of the rib, this improving the displacement of bone material in the critical range of larger diameters.

Figure 5:
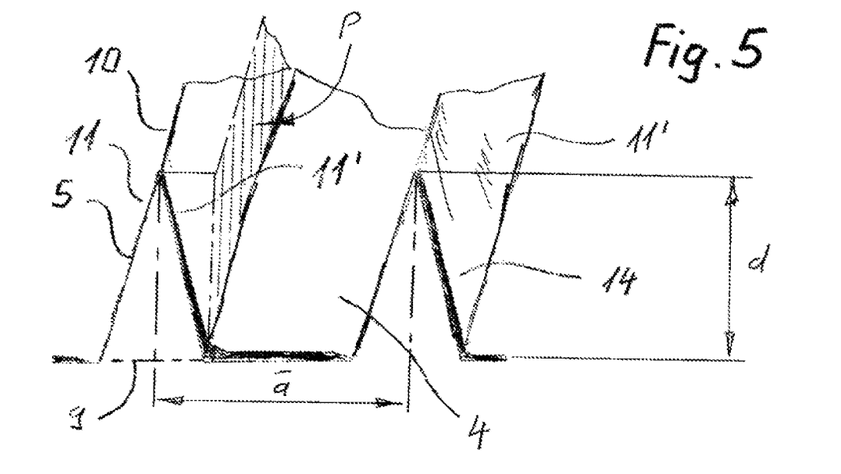
FIGS. 5 to 10: show greatly enlarged and schematic representations of various rib profiles.

FIG. 5 shows schematically two ribs 5 of identical cross-section with the rib foundation 9 and the rib vertex 10. The rib flanks 11, 11' meet in the rib vertex, therefore yielding a triangular shape in the cross-section transverse to the longitudinal extent of a rib. The rib height d is measured from the rib foundation 9 up to the rib vertex 10. In the exemplary embodiment depicted here, the rib flanks 11' inclined in the same direction are provided with an osteoinductive coating 14. It extends as far as into the region of the outer lateral surface 4 between two ribs. The interval a between two ribs, i.e., the interval from center to center rib foundation, is depicted again here for better understanding. Depicted here as representative of all exemplary embodiments is the flank projection area P of a rib, which is yielded by the rib height d and the rib length b, provided that the rib height stays constant and the rib has no interruptions.

Figure 6:
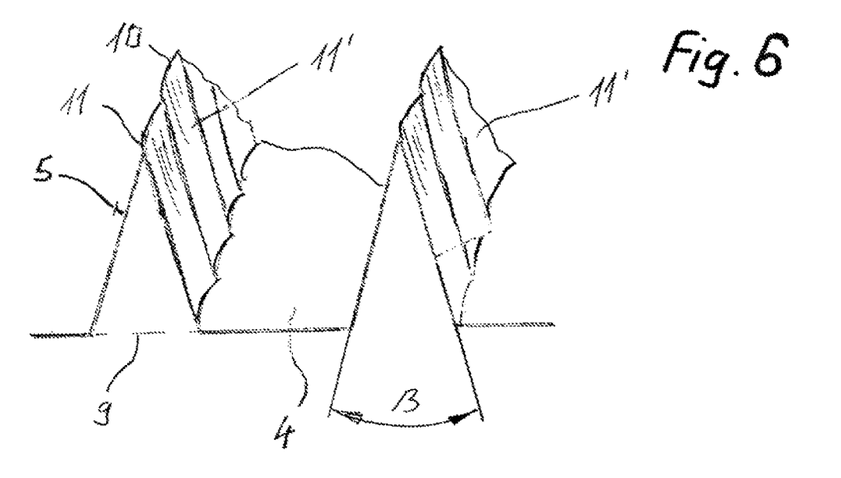

As per FIG. 6, the ribs 5 have a similar cross-sectional shape as in the case of the exemplary embodiment as per FIG. 5. In all exemplary embodiments, the flank angle β can be in the range from 10° to 90°.

The flank angle can either run in a constant manner or vary between the equator region and the near-pole region.

Instead of an osteoinductive coating, the rib flanks 11' inclined in the same direction are, as per FIG. 6, provided with a higher surface roughness in comparison with the opposite flanks 11, this being indicated by the faceted surface. The roughness value Ra can be, for example, less than 3 μm to 5 μm in the drive-in direction and greater than 30 μm in the pull-out direction. It is evidently possible to achieve the differing surface roughness with different processing methods, such as, for example, by one-sided machining, irradiation or coating of the respective rib flanks.

Figure 7:
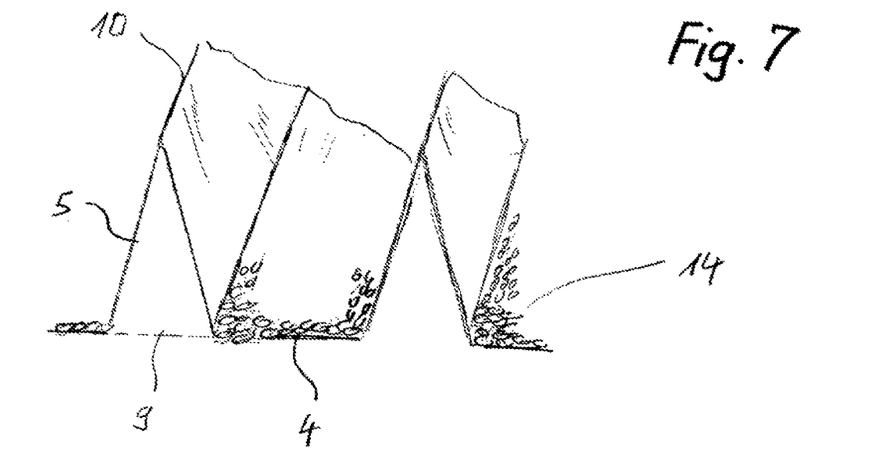

FIG. 7 shows one exemplary embodiment in which only the outer lateral surface 4 between two adjacent ribs 5 is provided with an osteoinductive coating 14.

Figures 8A, 8B:
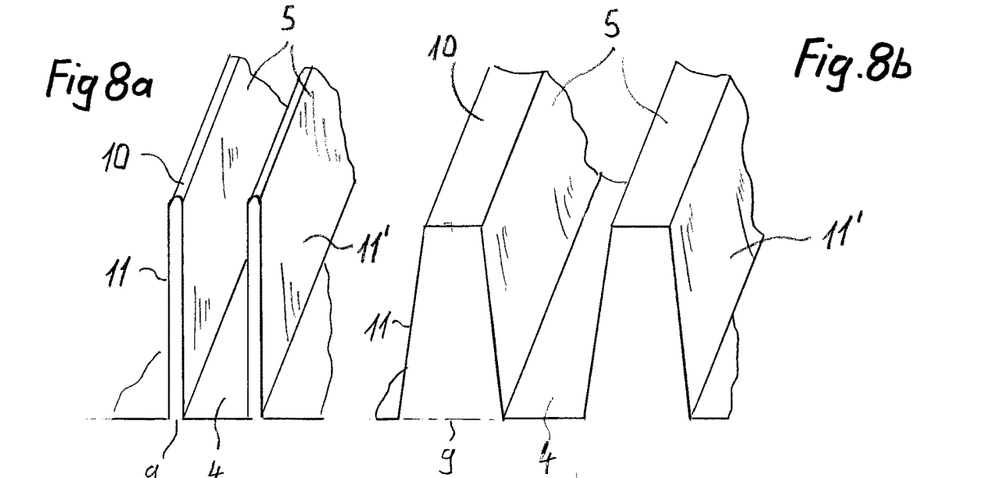

FIGS. 8a and 8b show exemplary embodiments in which the rib vertex does not run as a line, but in a flat manner or with slight curvature. As per FIG. 8a, the rib flanks 11, 11' run exactly or approximately in parallel, therefore forming ribs 5 which are lamellar or rectangular in cross-section. In contrast, the ribs 5 as per FIG. 8b have a configuration which is trapezoidal in cross-section and has a flat rib vertex 10.

Figure 9:
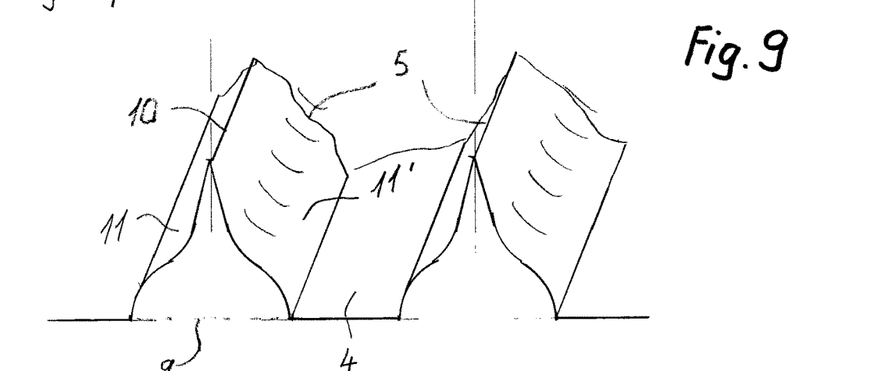

In the exemplary embodiment as per FIG. 9, the ribs 5 have a pagoda-shaped cross-section with a rather broad rib foundation 9 and an acute rib vertex 10. The rib flanks 11 and 11' run in a curved manner.

Figure 10:
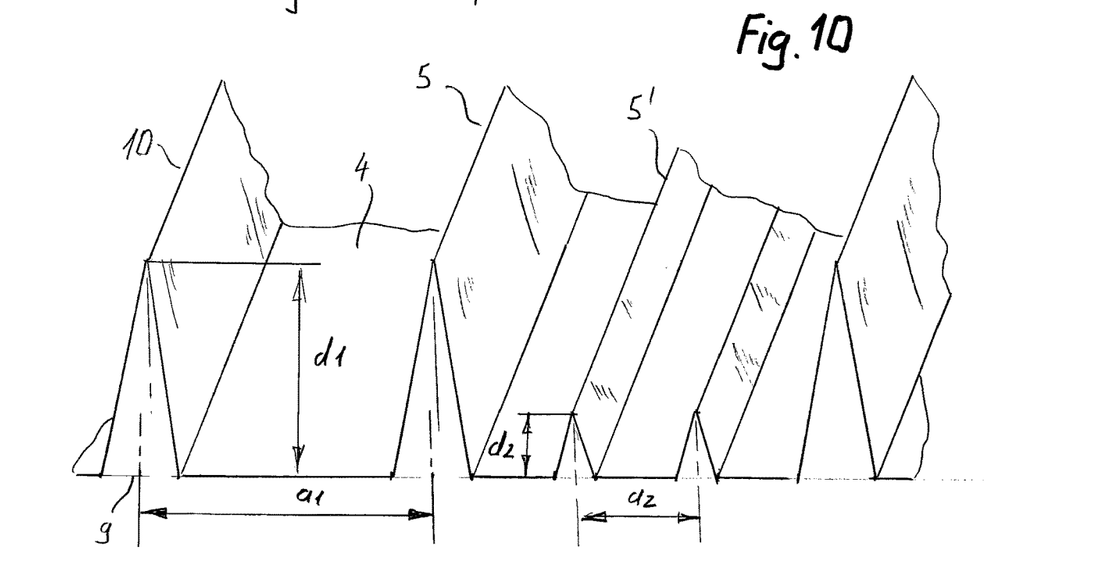

FIG. 10 shows schematically one exemplary embodiment having alternately arranged ribs 5 and 5' of differing height d1 and d2. The rib intervals a1 and a2 can also be correspondingly different.

Figure 11:
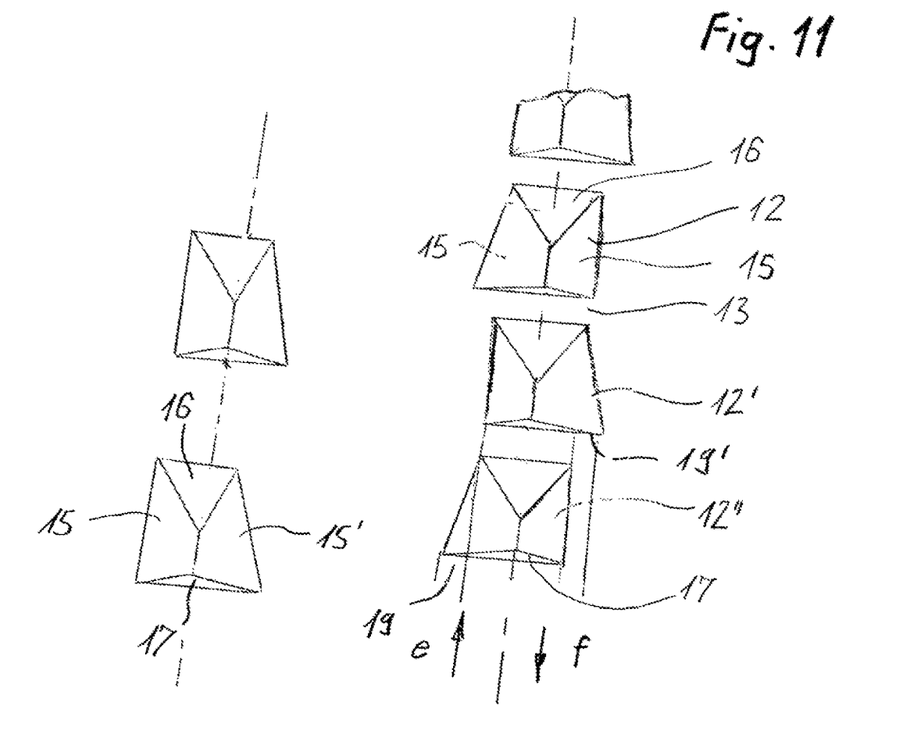
FIG. 11: shows a top view of rib teeth offset against one another.
Figure 12:
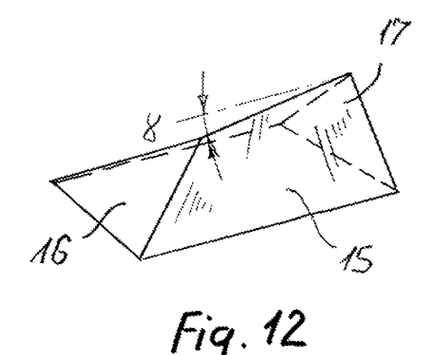
FIG. 12: shows a perspective view of an individual tooth.
Figure 13:
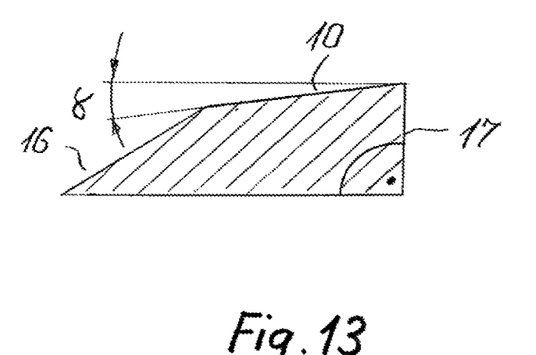
FIG. 13: shows a cross-section through the rib tooth as per

FIG. 11 shows a top view of individual rib teeth 12 which each represent irregular multisurface bodies, as additionally depicted in FIGS. 12 and 13. The rib teeth of the left row run in a regular manner and those of the right row run such that they are offset in relation to one another. Each rib tooth 12 has a quadrangular, especially trapezoidal, footprint, two teeth flanks 15, 15' inclined against one another, a pole side 16 and an equator side 17. The drive-in direction is depicted with the arrow e and the screw-out direction is depicted with the arrow f. The gaps 13 between the individual teeth are relatively small. The successive teeth 12' and 12" of the right row are offset against one another such that, based on the drive-in direction e, the footprint respectively projects to the right or to the left. As a result, sometimes the tooth flank 15 and sometimes the tooth flank 15' is somewhat further over the axis of symmetry of the total groove. The offset angle can be between 2° and 15°. This results in alternately protruding flanks 19, 19' which hamper the detachment of the joint socket in the screw-out direction f, since said flanks assume the function of barbs. By contrast, drive-in the drive-in direction e is not hampered by this configuration. Additionally contributing to this is the fact that the pole side 16 encloses an acute angle with the base, whereas the equator side 17 is approximately perpendicular to the base.

The table below shows, by way of example, the relationship between rib interval, rib height and number of ribs and the resultant cumulative flank projection area on three hip-joint shell sizes, 48 mm, 52 mm and 64 mm. A rib interval of 3 mm is regarded as ideal, this allowing a rib height of 1.1 mm. To this end, the cumulative flank projection areas achievable here are each specified in mm2. The remaining values are specified in mm. In addition, the number of ribs is also additionally specified, and also the ratios between the cumulative flank projection areas and the outer lateral surface.

|  | Min. | Ideal | Max. |
| --- | --- | --- | --- |
| Rip interval a | 0.2 | 3 | 4 |
| Rib height d | 0.1 | 1.1 | 4 |
| Parameters calculated on size 52 shell | | | |
| Outer lateral surface: 4412 mm2 | | | |
| Cum. flank projection area | 1416 | 1085 | 3270 |
| Number of ribs | 834 | 56 | 42 |
| Ratio | 0.32 | 0.25 | 0.74 |
| Parameters calculated on size 64 shell | | | |
| Outer lateral surface: 6637 mm2 | | | |
| Cum. flank projection area | 2127 | 1651 | 4846 |
| Number of ribs | 1022 | 70 | 52 |
| Ratio | 0.32 | 0.25 | 0.73 |
| Parameters calculated on size 48 shell | | | |
| Outer lateral surface: 3771 mm2 | | | |
| Cum. flank projection area | 1209 | 935 | 2909 |
| Number of ribs | 770 | 52 | 40 |
| Ratio | 0.32 | 0.25 | 0.77 |

Figure 14:
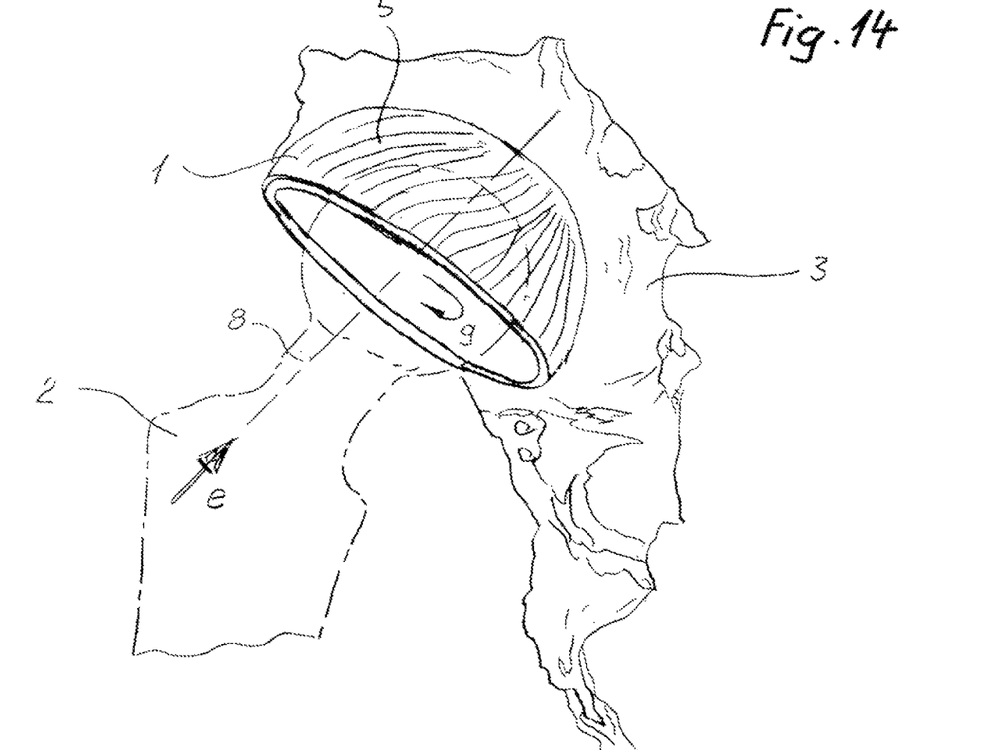

FIG. 14 shows a symbolic depiction of a prosthetic hip joint 2, of which the shaft with the joint ball is depicted in outline only. The hip-joint socket 1 with its ribs 5 has been driven into the acetabulum 3 in arrow direction e, said hip-joint socket carrying out a slight rotation in arrow direction g.

Figure 15:
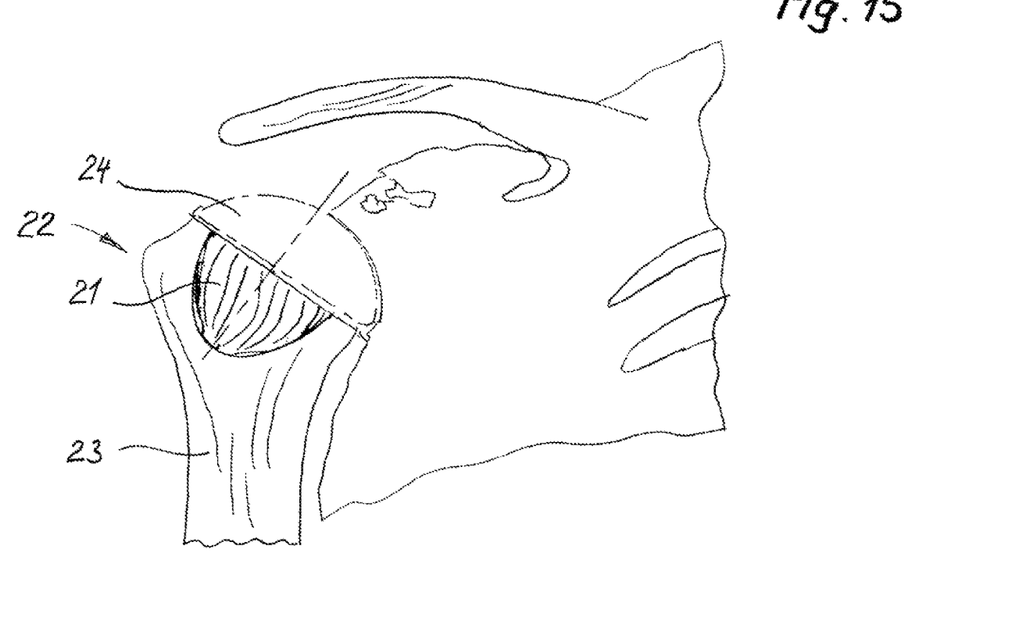
FIG. 15: shows the schematic representation of a prosthetic shoulder joint with humeral anchor.
Figures 16, 17, 18:
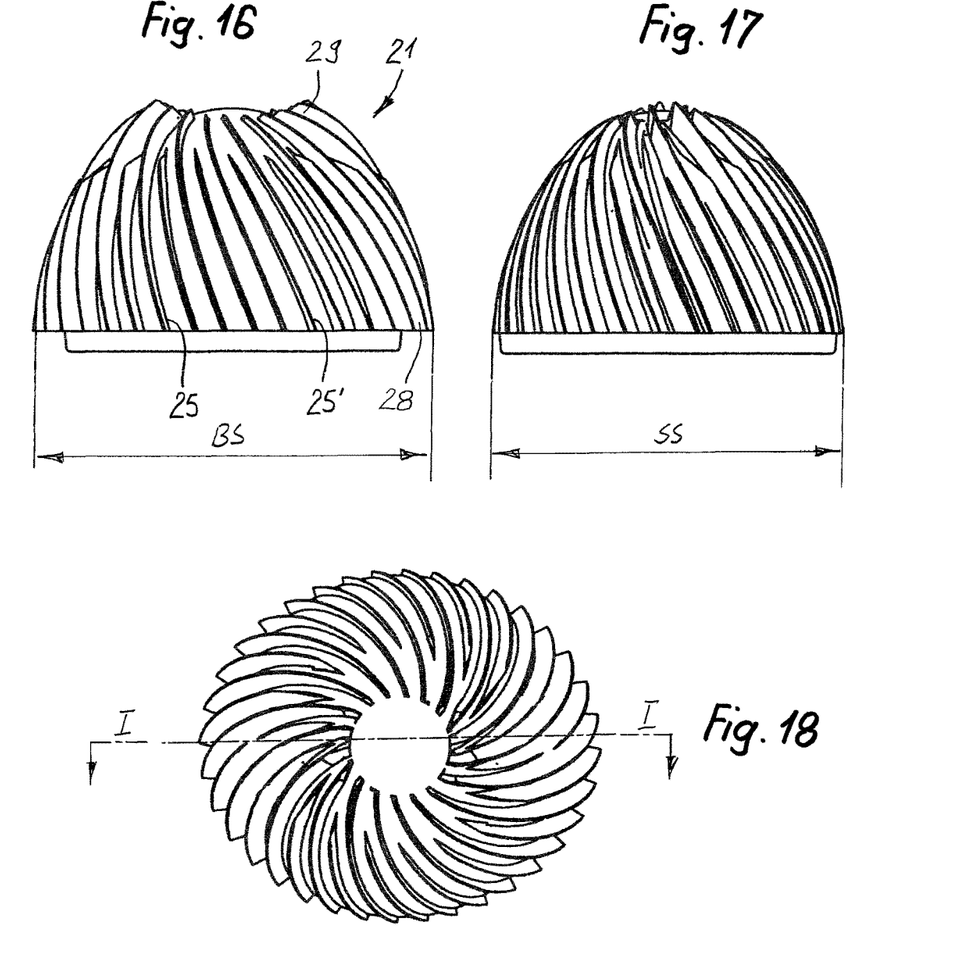
Figure 19:
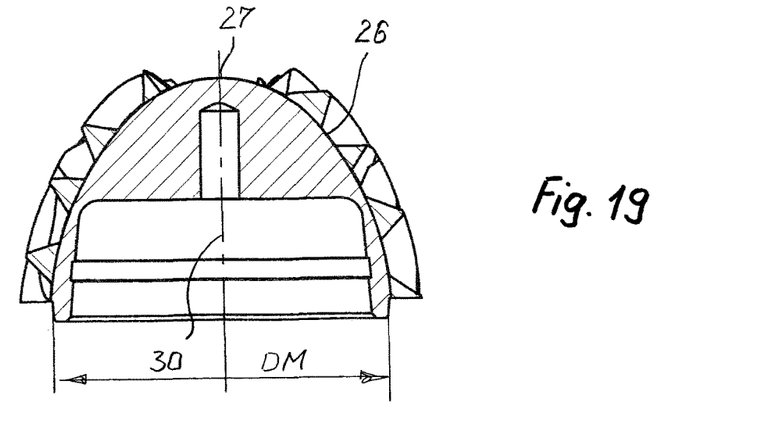

In contrast, FIG. 15 shows a symbolic depiction of a shaft-free prosthetic shoulder joint 22 in which the shell according to the invention is not a joint socket, but assumes the function of a humeral anchor 21 which has been driven into the humerus 23. In this case, the humeral head 24 connected to the humeral anchor assumes the function of the joint ball.

FIGS. 16 to 19 depict further details of a humeral anchor 21. What is striking in this case is the different shape of the cross-section and footprint in comparison with the hip-joint socket. As is evident especially from FIG. 19, the outer lateral surface 26 has a configuration which is ellipsoidal in cross-section and which has a rib-free, but closed, pole face 27. The individual ribs 25, 25' alternately extend up to the pole face or as far as a slight distance therefrom. Despite the ellipsoidal cross-section based on the longitudinal central axis, the shell has a circular shell shape at the equator. However, owing to the shell cross-section and the differing rib height at the equator of the individual ribs 25, 25', there is also an ellipsoidal outer footprint having a broad side BS and having a narrow side SS. As depicted, the individual ribs in the case of the humeral anchor preferably run in an uninterrupted manner, but with varying rib height and differing rib length in some cases. However, an interruption of individual ribs or all ribs to form individual teeth would be conceivable, too. Provided on the interior of the humeral anchor 21 are suitable fasteners 30 (FIG. 19) for fastening the humeral head following drive-in.

By analogy with the above-described hip-joint shell, what is depicted below, likewise by way of example, is a table with the relationships between rib interval, rib height and especially with the ratio between the cumulative flank projection area and the outer lateral surface. In this case, the shell sizes are, for a humeral anchor, naturally smaller than in the case of a hip-joint shell.

|  | Min. | Ideal | Max. |
|---|---|---|---|
| Rip interval a | 0.2 | 3 | 4 |
| Rib height d | 0.1 | 1.1 | 4 |
| Parameters calculated on size 28 shell Outer lateral surface: 1321 mm2 | | | |
| Cum. flank projection area | 517 | 426 | 1379 |
| Number of ribs | 456 | 32 | 24 |
| Ratio | 0.391 | 0.32 | 1.04 |
| Parameters calculated on size 38 shell Outer lateral surface: 2389 mm2 | | | |
| Cum. flank projection area | 935 | 739 | 2337 |
| Number of ribs | 614 | 42 | 32 |
| Ratio | 0.391 | 0.31 | 0.98 |
| Parameters calculated on size 47 shell Outer lateral surface: 3619 mm2 | | | |
| Cum. flank projection area | 1411 | 1115 | 3304 |
| Number of ribs | 754 | 52 | 38 |
| Ratio | 0.390 | 0.31 | 0.91 |

Figure 20:
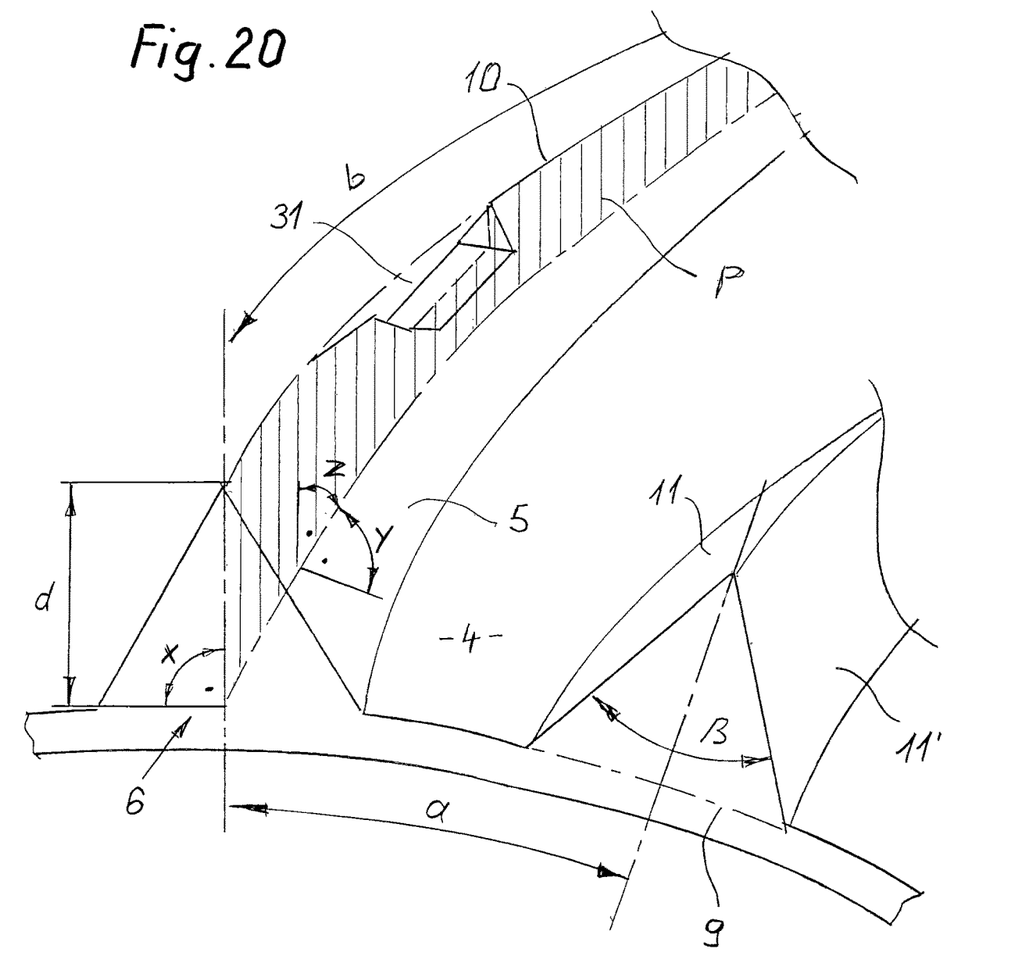

FIG. 20 shows again schematically and at great enlargement the flank projection area P using the example of a rib 5 having an interruption 31 in the rib vertex 10. However, said interruption does not reach as far as the rib foundation 9, there evidently being no interruption arising as a result, but merely a cutout in the flank projection area P. Here too, the rib length b corresponds to the longitudinal extent of the rib 5 from the equatorial end 6 up to the pole-sided end, which is not depicted here. The flank projection area P runs perpendicularly to the outer lateral surface 4, as indicated by the arrow x. Here, the rib flanks 11 and 11' form a wedge-shaped cross-section, specifically one based on a plane running perpendicularly to the longitudinal extent of the ribs and perpendicularly to the outer lateral surface, as indicated by the arrows y and z. This yields here the flank angle β. Here too, what is again depicted is the rib height d and the rib interval a as radian measure between the centers of adjacent ribs on the equator-sided rib foundation.

Figure 21:
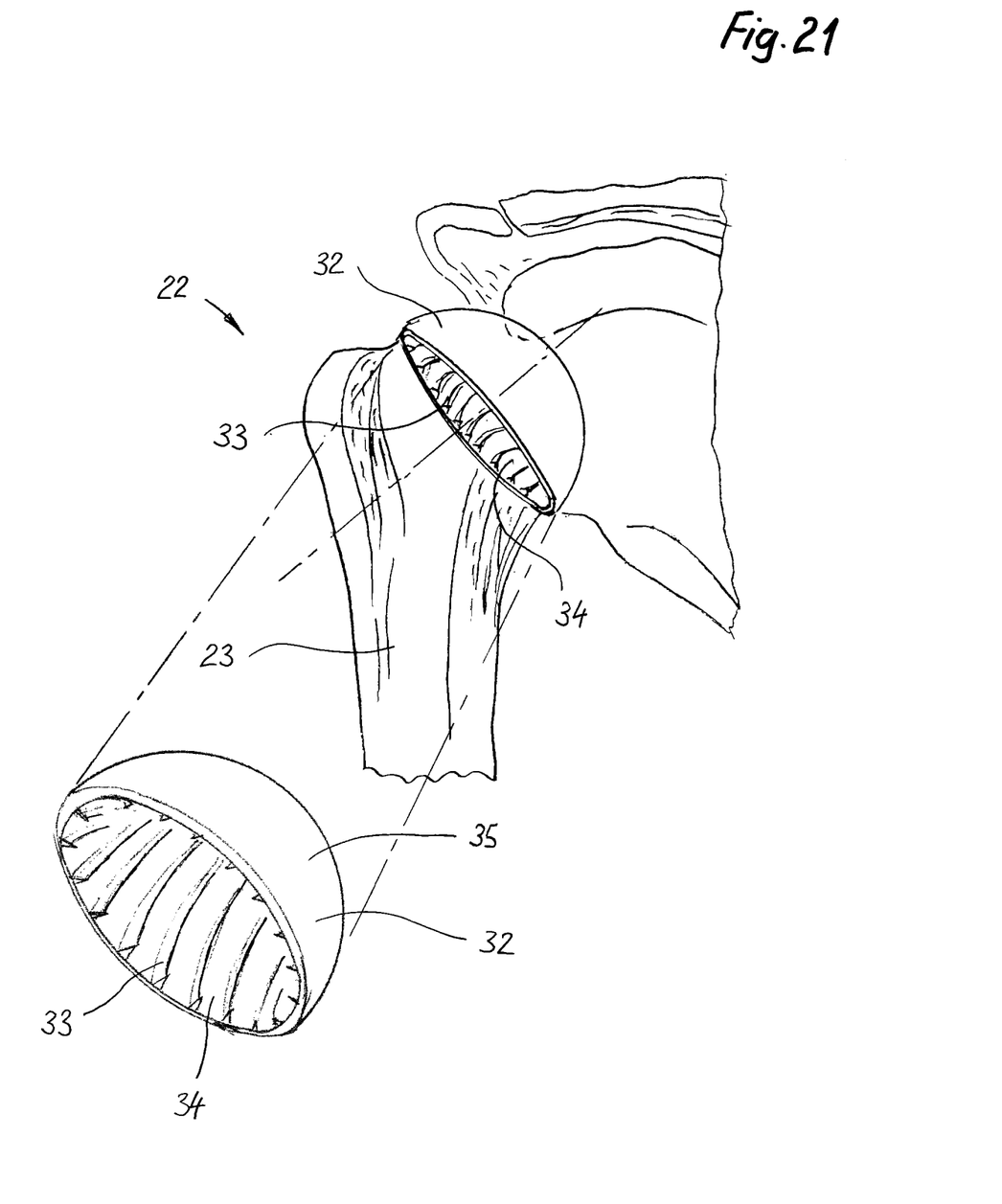
FIG. 21: shows the schematic representation of a prosthetic shoulder joint as surface replacement comprising an anchor-free joint shell.

FIG. 21 shows the example of a shell according to the invention, in which the ribs are not arranged on the outer lateral surface, but on an inner lateral surface. The example relates to a shaft-free prosthetic shoulder joint 22, wherein a hemispherical anchor shell 32 directly forms the surface replacement on the humerus 23. In contrast to the prosthetic shoulder joint as per FIG. 15, a humeral anchor is not required because the anchor shell 32 is directly driven onto the humerus by means of the inner ribs 33 and anchored thereon in this way. In this connection, the inner ribs 33 run on the inner lateral surface 34 toward the pole in the same manner as if the ribs were arranged on an outer lateral surface. In the present exemplary embodiment, the outer lateral surface 35 of the anchor shell 32 directly forms the joint surface, analogous to humeral head 24 in the case of the exemplary embodiment as per FIG. 15. When driving the anchor shell 32 onto the humerus 23, there is evidently likewise a rotation by a few angular degrees until the end position is reached.

Self-evidently, it would also additionally be possible to use a shell according to the invention for alternative joint constructions, for example for an inverse prosthetic shoulder in which the joint socket on the shoulder blade is replaced by an artificial joint ball and the joint ball on the upper arm is replaced by an artificial joint socket. In such a case too, it would be possible to anchor the joint socket in the humerus without a shaft.

The invention claimed is:

1. A shell to be driven into a bone substance for a prosthetic joint,
    having an outer lateral surface which is convexly curved, in cross-section, or
    having an inner lateral surface which is convexly curved,
    on which outer or inner lateral surface there is arranged a plurality of ribs,
    wherein all ribs extend in the same direction under a pitch angle from 45° to 85° at the equatorial end toward a pole-sided end on the outer lateral surface or on the inner lateral surface, and
    each rib has a flank projection area based on a plane running through a longitudinal extent of the rib and perpendicularly to the outer lateral surface or to the inner lateral surface, and a sum of the flank projection area of all ribs corresponds to at least one fifth of the entire outer lateral surface or the entire inner lateral surface.

2. The shell as claimed in claim 1, wherein said outer lateral surface or said inner lateral surface is spherical.

3. The shell as claimed in claim 1, wherein said pitch angle increases from the equatorial end toward the pole-sided end.

4. The shell as claimed in claim 1, wherein the ratio between the sum of the flank projection area of all ribs and the outer lateral surface or the inner lateral surface is in the range from 0.2:1 to 1:1.

5. The shell as claimed in claim 1, wherein at least 20 ribs are arranged on the outer lateral surface or on the inner lateral surface.

6. The shell as claimed in claim 1, wherein between 30 and 80 ribs are arranged on the outer lateral surface or on the inner lateral surface.

7. The shell as claimed in claim 1, wherein an interval between adjacent ribs, at the equatorial end from rib center to rib center on the outer lateral surface or on the inner lateral surface, is in the range from 0.2 mm to 4 mm.

8. The shell as claimed in claim 1, wherein at least 30% of the ribs extend over more than half a height of the shell, based on the longitudinal central axis thereof.

9. The shell as claimed in claim 1, wherein at least 50% of the ribs extend over more than half a height of the shell, based on the longitudinal central axis thereof.

10. The shell as claimed in claim 1, wherein ribs of differing length are arranged on the outer lateral surface or on the inner lateral surface.

11. The shell as claimed in claim 10, wherein the ribs of differing length are arranged in a regular sequence.

12. The shell as claimed in claim 1, wherein a rib height from a rib foundation to a rib vertex is in the range from 0.1 mm to 4 mm.

13. The shell as claimed in 1, wherein ribs of differing rib height are arranged on the outer lateral surface or on the inner lateral surface.

14. The shell as claimed in 13, wherein the ribs of differing rib height are arranged in a regular sequence.

15. The shell as claimed in claim 1, wherein ribs of differing rib height are arranged on a certain latitude based on a circumference of the outer lateral surface or the inner lateral surface.

16. The shell as claimed in claim 1, wherein the ribs have a cross-section which tapers from a rib foundation toward a rib vertex, based on a plane running perpendicularly to a longitudinal extent of the rib and perpendicularly to the outer lateral surface or to the inner lateral surface.

17. The shell as claimed in claim 16, wherein the ribs have a wedge-shaped cross-section.

18. The shell as claimed in claim 1, wherein opposing flank surfaces of the individual ribs have different roughness values such that the flanks subjected to a greater load during drive-in have a lower roughness value than the flanks subjected to a greater load during pull-out.

19. The shell as claimed in claim 1, wherein at least some of the ribs are interrupted to form individual rib teeth.

20. The shell as claimed in claim 19, wherein the rib teeth of a rib have a differing configuration between an equatorial end and a pole-sided end.

21. The shell as claimed in claim 19, wherein the rib teeth form irregular, multisurface bodies having a quadrangular footprint, two flank sides inclined against one another, a pole side facing the pole, and an equator side facing the equator.

22. The shell as claimed in claim 20, wherein the successive rib teeth of a rib are configured such that displacement of bone material takes place in a drive-in direction and an anchoring in the bone material takes place in a screw-out direction.

23. The shell as claimed in claim 19, wherein the gaps between the rib teeth do not extend as far as the outer lateral surface or the inner lateral surface.

24. The shell as claimed in claim 1, wherein at least one of said outer lateral surface or said inner lateral surface and the ribs is fully or partially provided with an osteoinductive coating.

25. The shell as claimed in claim 1, wherein the shell is a joint shell for a prosthetic hip joint to be driven into an acetabulum, and a ratio between the sum of the flank projection area of all ribs and the outer lateral surface is in the range from 0.2:1 to 0.8:1.

26. The shell as claimed in claim 1, wherein the shell is a humeral anchor to be driven into a humerus, and a ratio between the sum of the flank projection area of all ribs and the outer lateral surface is in the range from 0.3:1 to 1:1.

27. The shell as claimed in claim 1, wherein a course of the ribs is chosen such that each rotation by a predetermined angular value brings about a constant advance of the shell.

\* \* \* \* \*